United States Patent
Zielecka et al.

(10) Patent No.: US 9,126,839 B2
(45) Date of Patent: Sep. 8, 2015

(54) METHOD OF MANUFACTURING SILICA NANOPOWDERS WITH FUNGICIDAL PROPERTIES, ESPECIALLY FOR POLYMER COMPOSITES

(75) Inventors: Maria Zielecka, Warsaw (PL); Elżbieta Bujnowska, Warsaw (PL); Regina Jeziórska, Warsaw (PL); Krystyna Cyruchin, Warsaw (PL); Blanka Kepska, Mińsk Mazowiecki (PL); Magdalena Wenda, Radom (PL)

(73) Assignee: INSTYTUT CHEMI PRZEMYSLOWEJ IM. PROF. IGNACEGO MOSCICKIEGO, Warszawa (PL)

( * ) Notice: Subject to any disclaimer, the term of this patent is extended or adjusted under 35 U.S.C. 154(b) by 0 days.

(21) Appl. No.: 13/695,861

(22) PCT Filed: May 5, 2011

(86) PCT No.: PCT/PL2011/000047
§ 371 (c)(1),
(2), (4) Date: Nov. 2, 2012

(87) PCT Pub. No.: WO2011/139170
PCT Pub. Date: Nov. 10, 2011

(65) Prior Publication Data
US 2013/0045282 A1  Feb. 21, 2013

(30) Foreign Application Priority Data

May 7, 2010  (PL) .......................... 391169

(51) Int. Cl.
| | | |
|---|---|---|
| *A01N 59/20* | (2006.01) |
| *A01P 3/00* | (2006.01) |
| *C08K 5/5419* | (2006.01) |
| *C08K 5/5415* | (2006.01) |
| *C08K 5/5435* | (2006.01) |
| *C01B 33/145* | (2006.01) |
| *A61K 33/34* | (2006.01) |
| *C01B 33/146* | (2006.01) |
| *C01B 33/148* | (2006.01) |
| *C01B 33/18* | (2006.01) |

(52) U.S. Cl.
CPC .............. *C01B 33/145* (2013.01); *A01N 59/20* (2013.01); *A61K 33/34* (2013.01); *C01B 33/146* (2013.01); *C01B 33/148* (2013.01); *C01B 33/18* (2013.01)

(58) Field of Classification Search
CPC ...... A01N 25/12; A01N 59/20; C01B 33/146; C01B 33/148; C01B 33/18
See application file for complete search history.

(56) References Cited

U.S. PATENT DOCUMENTS

| 6,495,257 B1 | 12/2002 | Terase et al. |
| 2003/0235624 A1 | 12/2003 | Mangold et al. |
| 2007/0167554 A1* | 7/2007 | Ryang .......................... 524/492 |

FOREIGN PATENT DOCUMENTS

| WO | WO03070640 | 8/2003 |
| WO | WO2006049378 | 5/2006 |
| WO | WO2006084390 | 8/2006 |

OTHER PUBLICATIONS

Lin et al., J Therm Analysis and Calorimetry, 2012, abstract, 1 page.*
International Search Report for PCT/PL2011/000047 dated Aug. 4, 2011.
de Sales, "Optical characteristics of sol-gel silica containing copper" Materials Science and Engineering A-408 (2005) pp. 121-124.
PCT Written Opinion of the International Searching Authority for PCT/PL2011/000047.
Madler, L., "Controlled synthesis of nanostructured particles by flame spray pyrolysis," Aerolos Science 33 (2002), pp. 369-389.

* cited by examiner

*Primary Examiner* — Kyle Purdy
(74) *Attorney, Agent, or Firm* — Hoffman & Baron, LLP

(57) ABSTRACT

Method of manufacturing the silica nanopowders with fungicidal properties, consists in that the silica gel is obtained by sol-gel method from the reaction mixture containing tetraalkoxysilane and aliphatic alcohol, in the presence of ammonium compound, and thereafter the thermodegradable copper(II) salt a compound from the group of carbofunctional alkoxysilanes, and then, after evaporation of solvents the dry residue is heated at the decomposition temperature of copper (II) salt.

6 Claims, 1 Drawing Sheet

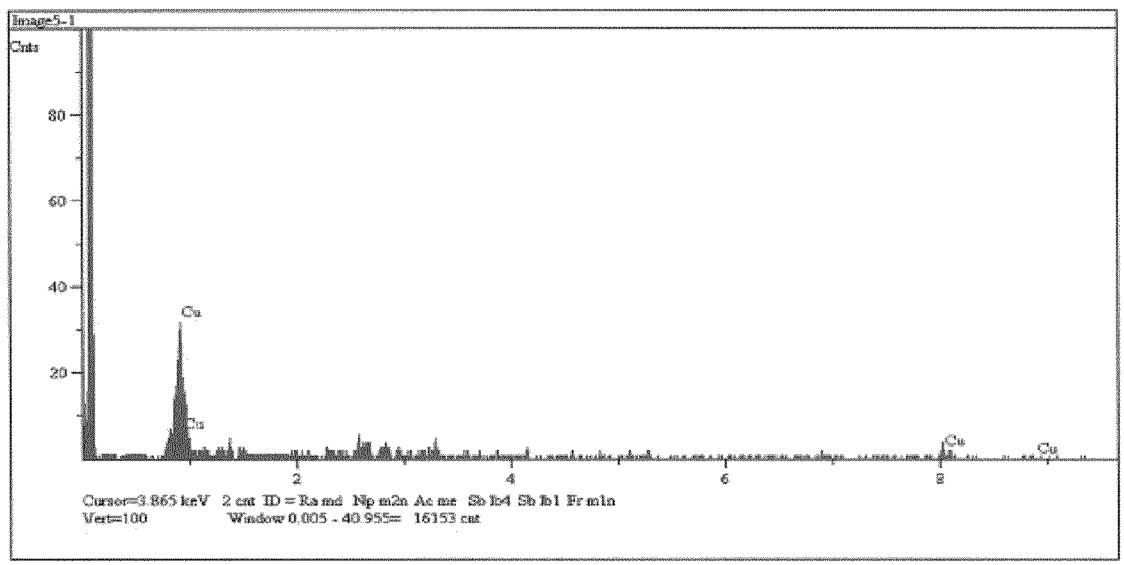

METHOD OF MANUFACTURING SILICA NANOPOWDERS WITH FUNGICIDAL PROPERTIES, ESPECIALLY FOR POLYMER COMPOSITES

CROSS-REFERENCE TO RELATED APPLICATIONS

This application is a National Phase application of International Application No. PCT/PL2011/000047 filed May 5, 2011 which claims priority to Polish Patent Application No. PL P-391169 filed May 7, 2010, the disclosures of which are incorporated herein by reference.

The invention relates to a method of manufacturing the silica nanopowders with fungicidal properties, especially for polymer composites.

The requirements for materials used in medicine, pharmacy, household goods, textile and wood industry, are the reason for the necessity of impart the mixtures of high molecular compounds with bactericidal and fungicidal properties.

One can find in the literature the information on the use of copper nanoparticles, e.g. as an additive for cellulose fibers (Grace Mary, S. K. Bajpai, Navin Chand; Journal of Applied Polymer Science; vol. 113 Issue 2, 757-766), with biocidal properties against *Escherichia coli*. It was stated in the publication of Nicola Cioffi, Luisa Torsi, Nicoletta Ditaranto, Giuseppina Tantillo, Lina Ghibelli, Luigia Sabbatini, Teresa Bleve-Zacheo, Maria D'Alessio, P. Giorgio Zambonin, Enrico Traversa; 2005 American Chemical Society; vol. 17 (21), 5255-5262 that the entire inhibition or slowing down the growth of living organisms, such as pathogenic fungi and microorganisms has occurred after use of the additive in the form of copper nanoparticles in polymer composites.

Copper nanoparticles have evidently higher biocidal activity than microparticles of that element. The substantial problem is the immobilization of copper nanoparticles in silica. Authors of the publication (T. Lutz, C. Estrournes, J. C. Merle, J. L. Guille (Optical properties of cooper-dopes silica gels; Journal of Alloys and Compounds 262-263 (1997) 438-442) claimed that one of the useful method is the implantation of ions with use of laser of appropriate wavelength (ultraviolet).

The use of nanopowders containing copper nanoparticles immobilized in silica, as components of nanocomposites and nanomaterials, is possible with the provision that they have reproducible and defined composition and chemical structure.

From the patent specification U.S. Pat. No. 6,495,257, there is known a method of manufacturing by sol-gel method, of spherical SiO2 particles containing nanoparticles of metal (inter alia Ag, Zn) oxides, introduced in the process of hydrothermal dispersing, consisting in stirring for several hours in a pressurized autoclave, at the temperature 185-200° C., the aqueous suspension of silica and metal oxides. The grain size of obtained powders is in the range of 1 to 200 μm. The described process does not solve the problem of obtaining silica nanopowders with the size below 200 nm, containing metal nanoparticles. It may lead to several restrictions connected with their use as nanofillers, e.g. in polymer composites.

BACKGROUND

The properties of polymer nanocomposites connected with the size of nanofiller particles are quite different from the properties of composites obtained with fillers with particles of the size above 200 nm. The use of just small amount of the nanofiller in polymer nanocomposites of an order of 0.5-6% permits to improve the mechanical, optical and barrier properties as well as higher chemical and thermal resistance. The coefficient of linear expansion and flammability decrease, which is advantageous for the final product. These results cannot be obtained with the use of standard amounts of the filler (ca. some dozen percent based on the whole composite).

SUMMARY

Method of manufacturing the silica nanopowders with fungicidal properties, by the sol-gel method of the invention is characterized in that the silica sol containing immobilized nanometric copper particles is prepared from the aqueous reaction mixture containing tetraalkoxysilane, in which the alkoxy group contains from C1 to C4 carbon atoms, alcohol or a mixture of aliphatic C1 to C4 alcohols in a mol ratio of from 1:5 to 1:35, in the presence of ammonium compound, used in an amount of from 0.001 to 0.05 mol per 1 mol of tetraalkoxysilane, by introducing, after the thorough mixing of components, the thermodegradable copper(II) salt in the form of aqueous solution in an amount of 0.0015-0.095 mol per 1 mol of tetraalkoxysilane, and with the addition of a compound from the group of carbo-functional alkoxysilanes, in an amount of 0.015-1 mol per 1 mol of copper(II) salt, and thereafter, after thorough mixing and the evaporation of solvents the dry residue is heated at the decomposition temperature of copper(II) salt.

Preferably, tetramethylammonium hydroxide or tetraethylammonium hydroxide is used as an ammonium compound.

Preferably, copper(II) acetate or copper(II) formate is used as copper(II) salt.

BRIEF DESCRIPTION OF THE FIGURES

FIG. 1 represents the X-ray dispersive spectroscopy (EDS-energy dispersive spectroscopy) pattern for silica nanopowders containing immobilized nanometric copper particles.

Preferably, γ-aminopropyltriethoxysilane or γ-glycidoxypropyltriethoxysilane is used as a compound from the group of carbo-functional alkoxysilanes.

DETAILED DESCRIPTION

The size of nanometric copper particles deposited by the process of the invention on the surface of nanopowder particles does not exceed 50 nm. Silica nanopowder containing immobilized copper particles of the process of the invention, of the particle size 48 nm are characterized with bulk density 86 g/l, and the bulk density of unmodified nanosilica of analogous particle size is 49.1 g/l (according to PE-EN 1097-3: 2000).

Silica nanopowders containing immobilized copper nanoparticles are characterized with biocidal activity, as it was show on the basis of microbiological tests by growth medium method on fluid media, performed in conditions of free access to nutritious substances. It was found that silica nanopowders containing immobilized nanometric copper particles show biocidal activity against mold fungi with the dose of 1.2 ppm. Non-modified silica nanopowders do not show fungicidal activity.

Silica nanopowders containing immobilized copper nanoparticles, obtained by the process of the invention, are storage stable, and the size of nanometric copper particles does not change.

The properties of obtained by the method of invention silica nanopowders, containing immobilized nanometric copper particles are important in the use of such powders as components of polymer composites, used in conditions favoring growth of fungi and molds. These may be, for example, composites containing cellulose fibers designed for the production wood-like moldings or packaging materials. Silica nanopowders, containing immobilized nanometric copper particles obtained by the method of invention can be used as additives for paints, varnishes, points used in rooms of higher hygienic requirements. They prevent the growth of mold fungi in moistened compartments: *Aspergillus fumigatus, Aspergillus ustus, Aspergillus sydowii, Penicllium verrucosum, Paecilomyces lilaceum* as well as bacteria of the genus *Pseudomonas, Bacillus* and the individual strains of *Alcaligenes faecalis, Staphylococcus xylosus, Aerococcus viridans, Acinetobacter juni/johnsoni, Achromobacter xyloxidans, Brevundimonas vesicularis, Stenotorphomonas maltophilia, Gemella haemolysans.*

The manufacturing of silica nanopowders containing nanometric copper particles on the surface, by the method of invention is illustrated in examples.

EXAMPLE I 160.1 g (3.47 mol) of anhydrous ethanol, 1.2 g of 25% aqueous solution of tetraethylammonium hydroxide (0.002 mol) and 55.2 g of distilled water was stirred by magnetic stirrer in an Erlenmeyer flask. The pH of the obtained mixture was 11.11. Subsequently, 21.3 g (0.10 mol) tetraalkoxysilane was added to the reaction mixture. In an early stage the reaction mixture was clear, but after 50 min the opalescence of the solution was observed. The contents of the flask was kept at ambient temperature and stirred for 2.5 h. On the basis of the analysis of obtained sol by photon correlation spectroscopy it was found that the size of sol particles was 50-56 nm. After 24 h 2.4 g of aqueous 0.1 mol solution of copper(II) acetate (0.00024 mol) and 0.00489 g γ-glycidoxypropyltriethoxysilane (0.000019 mol) were added to the reaction mixture. The whole mixture was stirred for 1 h. Thereafter the product was dried in the oven at the temperature of 90° C. for 1.5 h and heated at 250° C. for 2 h to decompose the copper acetate.

FIG. 1 presents the X-ray dispersive spectroscopy (EDS-energy dispersive spectroscopy) pattern permitting to perform the qualitative and quantitative analysis of the contents of metals, with visible peaks characteristic for copper.

The contents of copper, determined by atomic absorption spectroscopy was 0.0032 wt. %.

The so obtained silica powder, containing immobilized copper particles, was added in an amount of 5 wt. % to the polymer composite based on polycarbonate. On the basis of performed microbiological tests it was found that the obtained polymer composite containing 0.00016 wt. % (1.6 ppm) of copper nanoparticles immobilized on silica nanopowder had a biocidal activity against fungi *Aspergillus fumigatus, Aspergillus ustus, Aspergillus sydowii.*

EXAMPLE II 160.1 g (3.47 mol) of anhydrous ethanol, 0.47 g of 25% aqueous solution of tetraethylammonium hydroxide (0.002 mol) and 55.2 g of distilled water was stirred by magnetic stirrer in an Erlenmeyer flask. The pH of the obtained mixture was 11.39. Subsequently, 21.3 g (0.10 mol) tetraalkoxysilane was added to the reaction mixture. In an early stage, the reaction mixture was clear, but after 50 min the opalescence of the solution was observed. The contents of the flask was kept at ambient temperature and stirred for 2.5 h. On the basis of the analysis of obtained sol by photon correlation spectroscopy it was found that the size of sol particles was 75-80 nm. After 24 h 6.8 g of aqueous 0.1 mol solution of copper(II) formate (0.00069 mol) and 0.0106 g γ-aminopropyltriethoxysilane (0.000048 mol) were added to the reaction mixture. The whole mixture was stirred for 1 h. Thereafter, the product was dried in the oven at the temperature of 90° C. for 1.5 h and heated at 280° C. for 2 h to decompose the copper formate. The contents of copper, determined by atomic absorption spectroscopy was 0.006 wt. %. It was determined by scanning electron microscopy, that the obtained nanopowder consists of silica particles with the size of approximately 80 nm, containing immobilized copper nanoparticles.

The so obtained silica powder, containing immobilized copper particles, was added in an amount of 3 wt. % to the polymer composite based on polypropylene. On the basis of performed microbiological tests it was found that the obtained polymer composite containing 0.00025 wt. % (2.5 ppm) of copper nanoparticles immobilized on silica nanopowder had a biocidal activity against fungi *Penicllium verrucosum, Paecilomyces lilaceum.*

EXAMPLE III 160.1 g (3.47 mol) of anhydrous ethanol, 1.77 g of 25% aqueous solution of tetraethylammonium hydroxide (0.002 mol) and 55.2 g of distilled water was stirred by magnetic stirrer in an Erlenmeyer flask. The pH of the obtained mixture was 11.51. Subsequently, 21.3 g (0.10 mol) tetraalkoxysilane was added to the reaction mixture. In an early stage the reaction mixture was clear, but after 50 min the opalescence of the solution was observed. The contents of the flask was kept at ambient temperature and stirred for 2.5 h. On the basis of the analysis of obtained sol by photon correlation spectroscopy it was found that the size of sol particles was 100-120 nm. After 24 h 70.0 g of aqueous 0.1 mol solution of copper (II) acetate (0.007 mol) and 0.1397 g γ-aminopropyltriethoxysilane (0.00063 mol). The whole mixture was stirred for 1 h. Thereafter the product was dried in the oven at the temperature of 90° C. for 1.5 h and heated at 250° C. for 2 h to decompose the copper acetate. The contents of copper, determined by atomic absorption spectroscopy was 3.9 wt. %.

The so obtained silica powder, containing immobilized copper particles, was added in an amount of 0.3 wt. % to the polymer composite based on polyethylene. On the basis of performed microbiological tests it was found that the obtained polymer composite containing 0.00792 wt. % (79.2 ppm) copper nanoparticles immobilized on silica nanopowder had a biocidal activity against fungi *Penicllium verrucosum, Paecilomyces lilaceum, Aspergillus fumigatus, Aspergillus ustus, Aspergillus sydowii.*

EXAMPLE IV 189.23 g (4.10 mol) of anhydrous ethanol, 0.06 g 25% aqueous solution ammonia (0.0004 mol) and 48.75 g of distilled water was stirred by magnetic stirrer in an Erlenmeyer flask. The pH of the obtained mixture was 11.54. Subsequently, 28.2 g (0.13 mol) tetraalkoxysilane was added to the reaction mixture. In an early stage, the reaction mixture was clear, but after 13 min the opalescence of the solution was observed. The contents of the flask was kept at ambient temperature and stirred for 2.5 h. On the basis of the analysis of obtained sol by photon correlation spectroscopy, it was found that the size of sol particles was 180-190 nm After 24 h 73.0 g of aqueous 0.1 mol solution of copper(II) acetate (0.0073 mol) and 0.1457 g γ-glycidoxypropyltriethoxysilane (0.00058 mol). The whole mixture was stirred for 1 h. Thereafter, the product was dried in the oven at the temperature of 90° C. for 1.5 h and heated at 250° C. for 2 h to decompose the copper acetate. The contents of copper, determined by atomic absorption spectroscopy was 4.5 wt. %.

The so obtained silica powder, containing immobilized copper particles, was added in an amount of 1.5 wt. % to the polymer composite based on polyamide 6. On the basis of performed microbiological tests it was found that the obtained polymer composite containing 0.07 wt. % (700 ppm) copper nanoparticles immobilized on silica nanopowder had a biocidal activity against fungi *Penicllium verrucosum, Paecilomyces lilaceum, Aspergillus fumigatus, Aspergillus ustus, Aspergillus sydowii*.

EXAMPLE V 156.2 g (3.39 mol) of anhydrous ethanol, 0.5 g 25% aqueous solution ammonia (0.0036 mol) and 36.8 g of distilled water was stirred by magnetic stirrer in an Erlenmeyer flask. The pH of the obtained mixture was 11.49. Subsequently, 20.03 g (0.09 mol) tetraalkoxysilane was added to the reaction mixture. In an early stage the reaction mixture was clear, but after 25 min the opalescence of the solution was observed. The contents of the flask was kept at ambient temperature and stirred for 2.5 h. On the basis of the analysis of obtained sol by photon correlation spectroscopy, it was found that the size of sol particles was 140-160 nm After 24 h, 77.0 g of aqueous 0.1 mol solution of copper(II) acetate (0.008 mol) and 1.597 g γ-aminopropyltriethoxysilane (0.0072 mol). The whole mixture was stirred for 1 h. Thereafter, the product was dried in the oven at the temperature of 90° C. for 1.5 h and heated at 250° C. for 2 h to decompose the copper acetate. The contents of copper, determined by atomic absorption spectroscopy was 3.5 wt. %.

The so obtained silica powder, containing immobilized copper particles, was added in an amount of 0.75 wt. % to the polymer composite based on polyethylene terephthalate. On the basis of performed microbiological tests it was found that the obtained polymer composite containing 0.09 wt. % (900 ppm) copper nanoparticles immobilized on silica nanopowder had a biocidal activity against fungi *Penicllium verrucosum, Paecilomyces lilaceum, Aspergillus fumigatus, Aspergillus ustus, Aspergillus sydowii*.

What is claimed is:

1. A method of manufacturing silica nanopowders with fungicidal properties, by the sol-gel method, comprising:
    forming and mixing an aqueous reaction mixture comprising tetraalkoxysilane and an ammonium compound, wherein the tetraalkoxysilane comprises an alkoxy group that contains from C1 to C4 carbon atoms, alcohol or a mixture of aliphatic C1 to C4 alcohols in a mol ratio of from 1:5 to 1:35, and wherein the ammonium compound is used in an amount of from 0.001 to 0.05 mol per 1 mol of tetraalkokxysilane;
    adding a carbo-functional alkoxysilane and a thermodegradable copper(II) salt in the form of an aqueous solution to the aqueous reaction mixture, wherein the thermodegradable copper(II) salt has a decomposition temperature and is added in an amount of 0.0015-0.095 mol per 1 mol of tetraalkokxysilane, and wherein the carbo-functional alkoxysilane is added in an amount of 0.015-1 mol per 1 mol of thermodegradable copper(II) salt;
    mixing the aqueous reaction mixture;
    drying the aqueous reaction mixture to evaporate solvents and form a dry residue; and
    heating the dry residue at a temperature of at least 250° C. to decompose the thermodegradable copper(II) salt and form nanopowders with fungicidal properties containing immobilized nanometric copper particles.

2. The method of claim 1, wherein tetramethylammonium hydroxide or tetraethylammonium hydroxide is used as an ammonium compound.

3. The method of claim 1, wherein copper(II) acetate or copper(II) formate is used as the thermodegradable copper (II) salt.

4. The method of claim 1, wherein γ-aminopropyltriethoxysilane is used as the carbo-functional alkoxysilane.

5. The method of claim 1, wherein γ-glicydoxypropyltriethoxysilane is used as the carbo-functional alkoxysilane.

6. The method of claim 1, wherein the size of the nanometric copper particles is 50 nm or less.

\* \* \* \* \*